United States Patent
Cestaro et al.

(10) Patent No.: US 6,340,669 B1
(45) Date of Patent: Jan. 22, 2002

(54) LIPOPROTEIN COMPLEXES AND COMPOSITIONS CONTAINING THEM

(75) Inventors: Benvenuto Cestaro; Elvira Pistolesi, both of Milan (IT)

(73) Assignee: Hunza di Maria Carmela Marazzita S.A.S., Milan (IT)

( * ) Notice: Subject to any disclaimer, the term of this patent is extended or adjusted under 35 U.S.C. 154(b) by 0 days.

(21) Appl. No.: 09/646,620

(22) PCT Filed: Jan. 21, 2000

(86) PCT No.: PCT/EP00/00452

§ 371 Date: Sep. 20, 2000

§ 102(e) Date: Sep. 20, 2000

(87) PCT Pub. No.: WO00/43036

PCT Pub. Date: Jul. 27, 2000

(30) Foreign Application Priority Data

Jan. 22, 1999 (IT) .......................................... MI99A0114
Nov. 26, 1999 (IT) .......................................... MI99A2471

(51) Int. Cl.[7] .......................... A61K 38/00; C07K 1/00; C07K 5/00; C07K 7/00
(52) U.S. Cl. .......................... 514/21; 514/12; 530/359; 530/300; 530/350; 530/345
(58) Field of Search ................................ 514/2, 21, 12; 530/300, 345, 350, 359

(56) References Cited

U.S. PATENT DOCUMENTS 5,411,956 A   5/1995   Miyazaki et al.
5,643,874 A   7/1997   Bremer et al.

FOREIGN PATENT DOCUMENTS

DE   24 00 518   7/1975
DE   297 08 250   7/1997
EP   0 451 436   10/1991

OTHER PUBLICATIONS

J. Agric. Food Chem., 1994, 42, 2382–2385, "Purification and Characterization of Proteinous Inhibitor of Lipase from Wheat Flour", H. Tani et al.

Life Sciences, vol. 58, No. 20, pp. 1745–'755, 1996, Globin Digest, Acidic Protease Hydrolysate, Inhibits Dietary Hypertriglyceridemia and Val–Val–Tyr–Pro, etc., K. Kagawa et al.

Journal of Lipid Research, vol. 25, 1984, pp 1214–1221, "Studies on the inhibition of pancreatic and microbial lipases by soybean proteins", Y. Gargouri et al.

Agr. Biol. Chem., 38(1), 97–101, 1974, "Characterization of Inhibitor Protein for Lipase in Soybean Seeds", K. Satouchi et al.

The Journal of Biological Chemistry, vol. 260, No. 4, Issue of Feb. 25, pp. 2268–2273, "Inhibition of Lipases by Proteins A Kinetic Study with Dicaprin Monolayers", Y. Gargouri et al.

Biochimica et Biophysica Acta, 391 (1975), 170–178, "Inhibition of Amylases from Different Origins by Albumins from the Wheat Kernel", V. Silano et al.

Biochimica et Biophysica Acta, 422 (1976), 159–169, "Purification and Properties of An Alpha–Amylase Inhibitor From Wheat", M. O'Donnell et al.

The Journal of Biological Chemistry, vol. 250, No. 20, Issue of Oct. 25, pp. 8030–8037, 1975, Purification and Properties of Phaseolamin, an Inhibitor of Alpha–Amylase, from the Kidney Bean . . . , J. Marshall et al.

Ernahrung/Nutrition, vol. 22/NR 4 (1998), pp. 148–153, "Protein–Inhibitors of Digestive Enzymes: Risk Factor and Change in our Nutrition", A. Taeufel, XP–000929116.

Proceedings of the Nutrition Society (1991), 50, pp. 399–408, "Modification of energy density with inhibitors of carbohydrate and fat digestion", R. H. Taylor, XP–000929121.

*Primary Examiner*—Avis M. Davenport
(74) *Attorney, Agent, or Firm*—Griffin & Szipl, P.C.

(57)   ABSTRACT

Lipoprotein complexes comprising a lipase-inhibiting protein component, and/or amylase-inhibiting protein component and a phospholipid component, compositions containing said complexes in combination with a polysaccharide component, pharmaceutical formulations and foods containing said complexes or compositions, processes for the preparation of said complexes and compositions, which are capable of reducing the weight increase following hypercaloric diets and of exerting hypocholesterolemizing, hypotriglyceridemizing and antioxidizing activities.

30 Claims, No Drawings

LIPOPROTEIN COMPLEXES AND COMPOSITIONS CONTAINING THEM

The present invention relates to a lipoprotein complex at the same time formed by one or more protein fractions from animal and/or vegetable sources (and/or peptides obtained by hydrolysis of the proteins themselves) together with one or more phospholipid species, as well as to pharmaceutical and dietetic compositions, and food containing said lipoprotein complex.

More particularly, the present invention relates to a lipoprotein complex comprising:
a lipase-inhibiting protein or peptide component, and/or
an amylase-inhibiting protein or peptide component, and
a phospholipid component.

More specifically, the present invention relates to compositions of lipase- and/or amylase- inhibiting proteins and phospholipids as well as to compositions of fibers, lipase- and/or amylase- inhibiting proteins and phospholipids, which surprisingly proved to reduce the weight increase following hypercaloric diets, while exerting effective hypocholesterolemizing, hypotriglyceridemizing and antioxidant activities. These surprising activities of the lipoprotein complexes can further be enhanced by combining them with polysaccharide matrices consisting of one or more species of vegetable and/or animal fibers.

Some specific proteins (and/or some peptides obtained by hydrolysis therefrom) capable of inhibiting the activities of lipases and amylases (the enzymes capable of promoting digestion and therefore the absorption and bioavailability of fats and carbohydrates which recognizedly are the main source of calories for human body), have been studied and identified in common food, both from animal and vegetable sources. In view of these evidences, these protein purified fractions and/or peptides therefrom can be used for the treatment of overweight and obesity. Known examples of lipase-inhibiting proteins and/or peptides are:

a) the protein and/or peptide fractions extracted from wheat flour according to the procedures by H. Tani et al. (1994, J. Agric. Food Chem., vol. 42, page 2382)
b) the globin protein and/or peptide fractions extracted and purified from animal erythrocytes and tested according to the procedures by K. Kayawa et al. (1996, Life Sci, vol. 58 n. 20, page 1745)
c) the protein and/or peptide fractions extracted and purified from soy-bean and tested according to the procedures by Gargouri Y. et al. (1984, J. Lipid Res., vol. 25, page 1214) and by K. Satouchi et al. (1974, Agr. Biol. C 38, 1, page 97)
d) the protein and/or peptide fractions deriving from animal or egg serum albumins, from animal lactoglobulins and myoglobins obtained and tested according to the procedures by Gargouri Y. et al. (1985, J. Biol. Chem., vol. 260 n. 4, page 2268)

Examples of amylase-inhibiting proteins and/or peptides are:
a) the protein and/or peptide fractions of vegetable albumins extracted from the caryopsis of a number of cereals, in particular wheat and barley, and tested according to the procedures by Silano V. et al. (1975, Biochim. Biophys. Acta, vol. 391, page 170) and by O'Donnell M. D. et al. (1976, Biochim. Biophys. Acta, vol. 422, page 159)
b) the protein and/or peptide fractions extracted from leguminous plants, in particular bean, and tested according to the procedures by Marshall J. T. et al. (1975, J. Biol. Chem., vol. 250 n. 20, page 8030).

Furthermore, a number of dietetic preparations for the control of overweight are already marketed which make use of one or more of the above cited protein and/or peptide components capable of inhibiting the activities lipases and/or the amylases, selected from those described above and used together with other widely known, already used nutrients capable promoting the control of overweight, such as different species of fibres, some minerals, vitamins, etc.

Examples of these commercial preparations are:
a) Half Sitoal by Nihon Clinic (Japan)
b) Napple by Hankyu Kyoei Bussan (Japan)
c) Sweet Cut Diet by Tokyo Nagai (Japan)
d) Triple Block by Yuuki System (Japan)
e) Fast Slim Ladia by Kenbisha (Japan)
f) Peptide FM by Strength System (Germany)
g) Citrisan by Swedish Makronova AB (Sweden)
h) Bean Rep by Cheil Food & Chemical (South Korea)
i) Allure, after dinner tablets by Kernpharm-Ultra Vit. BV (the Netherlands)
l) Fat cut by Sentose (Taiwan)
m) Oligo Peptide by Pharmafood (The Netherlands).

The present invention surprisingly proved that lipoprotein complexes containing one or more of these protein components (or the peptides obtained by hydrolysis of these proteins), having inhibiting activity on digestive lipases and amylases, together with a phospholipid component from animal and/or vegetable sources, are an effective, well tolerated nutritional supplement capable of reducing simultaneously and with a surprising synergism: a) overweight and obesity; b) hypercholesterolemia; c) hypertriglyceridemia and d) increased formation of plasma and tissue peroxides in animals and humans following hypercaloric and/or unbalanced diets. Preferably, the lipase-inhibiting protein or peptide component is 10 to 40% by weight of the lipoprotein complex, the amylase-inhibiting component is 10 to 40% and the phospholipid component is 20 to 80% by weight of said complex.

Non-limiting examples of protein. fractions (and/or of peptides obtained by hydrolysis of said proteins) are the already listed preparations of proteins of vegetable and/or animal origin.

Non-limiting examples of phospholipid components from animal and/or vegetable sources are phosphatidylcholine, phosphatidylethanolamine, mono- and dimetilphosphatidylethanolamine, phosphatidylserine, phosphatidylinositol and derivatives, phosphatidylglycerol, cardiolipins, lysophospholipid analogues of the compounds mentioned above and/or mixtures thereof.

The lipoprotein complexes should be administered in a daily amount such as to reach an intake of 0.01–2000 mg, preferably 5–100 mg, of proteins per kg body weight and of 0.01–1000 mg, preferably 5–100 mg, of phospholipids per kg body weight.

The present inyention also relates to compositions obtained by combining the above cited lipoprotein complexes with a polysaccharide component selected from the group consisting of starches and flours, celluloses, chitins and chitosans, pectins, inulins, lignins and derivatives, cyclodextrins and derivatives, and mixtures thereof.

The present invention further relates to the pharmaceutical compositions (tablets, sugar-coated pills, lozenges, chewable tablets, effervescent tablets, syrups, chewing gums, etc.) as well as the various foods (bread, pasta, crackers, pizzas, pies, biscuits, juices, soft drinks, milk and derivatives, honey, butter and margarine, dressings and seasonings, mayonnaise, creams, and the like) containing the lipoprotein complexes and the compositions mentioned above, for the oral administration.

Finally, the invention relates to a process for the preparation of both the lipoprotein complexes as such and the compositions including the polysaccharide component.

The advantages of the complexes and compositions according to the present invention will be further evidenced by the following examples.

EXAMPLE 1

Lipoprotein Complexes Consisting of a) 50 g of lipase-inhibiting proteins from soy-bean, obtained according to the method by K. Satouchi et al. (1974; Agr. Biol. Chem.; 38 (1); page 97). In short, soy-bean dried cotyledons are ground and homogenised in 0.1 M Tris-HCl buffer at pH 7.4 containing 1 mM Ca-acetate. The homogenate is centrifuged at 10.000×g for 30 min and the supernatant is fractioned by addition of ammonium sulfate. The fraction precipitated at 0.25–0.50% of ammonium sulfate is dialysed against buffer and dried, to obtain the crude fraction of lipase-inhibiting proteins.

b) 20 g of amylase-inhibiting proteins from bean, obtained according to the method by J. T. Marshall et al. (1975; J. Biol. Chem., 250 n. 20; page 8030). In short, the bean flour obtained by milling is extracted at room temperature with a NaCl aqueous solution (1%). The resulting extract is centrifuged at 20.000×g for 30 min and the supernatant is heated at 70° C. for 15 min. The coagulated proteins are removed by centrifugation at 20.000×g for 30 min and the supernatant is dialysed against $H_2O$ at 4° C. for 12 hours and then dried to obtain the crude fraction of amylase-inhibiting proteins.

c) 100 g of commercial soy-bean lecithins containing 40% of phosphatidylcholine, 35% of phosphatidylethanolamine, 18% of phosphatidylinositol and smaller amounts of other phospholipids, such as phosphatidylserine, phosphatidic acid, phosphatidylglycerol and lysophospholipids. The soy-bean lecithins are dissolved in hexane and placed in a rotary evaporator containing glass microbeads of 1–2 mm diameter, the solvent is evaporated off under vacuum at 25° C. to obtain a film of phospholipid monomers adhered to the glass microbeads. An aqueous solution buffered to physiological pH and containing the lipase- and amylase-inhibiting proteins is added to the microbeads coated with phospholipid monolayers and is subjected to mild stirring for 30 min at 250° C.

The solution progressively becomes cloudy as the lipoprotein complexes form, then is centrifuged at 3000×g for 5 min to separate the glass microbeads; the resulting supernatant is then spray-dried to a powder. Said powder is the lipoprotein complex and can be used as such both for the preparation of the pharmaceutical (or dietetic) compositions and for the preparation of the various foods.

EXAMPLE 2

Lipoprotein Complexes Consisting of a) 160 g of commercial lipase-inhibiting proteins (Peptide FM of DMV International, Veghel, The Netherlands);

b) 40 g of amylase-inhibiting proteins from bean obtained according to the process reported in example 1b above;

c) 400 g of soy-bean lysolecithins obtained by hydrolysis of lecithins having composition similar to that reported in example 1c above.

The soy-bean lysolecithins are dissolved in hot ethanol (0.5 litres) and the ethanol solution is injected under pressure into 5 litres of an aqueous solution buffered to physiological pH containing the lipase- and amylase-inhibiting proteins and subjected to continuous stirring for 15 min at 2° C. The water-alcoholic solution of lysolecithins and proteins progressively becomes cloudy as the lipoprotein complexes form, then is spray-dried to a powder. Said powder is the lipoprotein complex and can be used as such both for the preparation of the pharmaceutical (or dietetic) compositions and for the preparation of the various foods.

EXAMPLE 3

Composition Containing Lipoprotein Complexes in Combination with a Polysaccharide Component, Consisting of a) 80 g of commercial lipase-inhibiting proteins as in example 2a above;

b) 20 g of commercial amylase-inhibiting proteins (Bean protein concentrate by Sochim International, Milano—Italy);

c) 100 g of commercial egg lecithins containing above 50% of phosphatidylcholine, above 35% of phosphatidylethanolamine and smaller amounts of other phospholipids such as phosphatidylinositol, phosphatidylserine, phosphatidylglycerol, phosphatidic acid and lysophospholipids;

d) 100 g of fibers: 40 g of chitosan, 40 g of oat fibers and 20 9 of cypress lignin.

The lipoprotein complexes of the lipase- and amylase-inhibiting proteins with the egg phospholipids are prepared in water-alcoholic solution as already described in example 2 above. This water-alcoholic solution is subsequently added with oat fibers, chitosan and the lignins under stirring at 25° C. for 15 min. The resulting final solution is spray-dried to a powder. Said powder can be used as such both for the preparation of the pharmaceutical (or dietetic) formulations and for the preparation of the various foods.

EXAMPLE 4

Composition Containing Lipoprotein Complexes in Combination with a Polysaccharide Component, Consisting of a) 50 g of lipase-inhibiting proteins from soy-bean prepared as reported in example 1a above;

b) 50 g of amylase-inhibiting proteins from bean prepared as reported in example 1b above;

c) 200 g of commercial soy-bean lecithins having composition similar to that reported in example 1c above;

d) 500 g of wheat flour.

Using a process similar to that described in example 3 above, a powder composition is obtained which can be used as such both for the preparation of the pharmaceutical (or dietetic) formulations and for the preparation of the various foods.

EXAMPLE 5

Lipoprotein Complexes Consisting of a) 100 g of lipase-inhibiting proteins, consisting of a mixture of 50 g of peptides WGE 80 GPU and 50 g of peptides EE 90 FX (by DMV International, Veghel, The Netherlands);

b) 100 g of commercial soy lecithins containing 40% of phosphatidylcholine, 35% of phosphatidylethanolamine, 18% of phosphatidylinositol and smaller amounts of other phospholipids, such as phosphatidylserine, phosphatidic acid, phosphatidylglycerol and lysophospholipids. The powdered lipase-inhibiting proteins and lecithins are mechanically mixed and suspended in an aqueous solution buffered to physiological pH. The solution progressively becomes cloudy as the lipoprotein complexes form is then spray-dried to a powder. Said powder is the lipoprotein complex and can be used as such both for the preparation of the pharmaceutical (or dietetic) compositions and for the preparation of the various foods.

Pharmacological and/or Dietetic Tests

In order to study the pharmacological and/or dietetic characteristics of the compositions according to the invention, a series of tests were carried out on rats.

In these tests, rats were administered with hypertriglyceridemizing and hypercholesterolemizing hypercaloric diet; after 20 day treatment the following parametres were evaluated:

1°) Effect of the composition on body weight increase;
2°) Effect of the composition on total cholesterol plasma levels;
3°) Effect of the composition on HDL cholesterol plasma levels;
4°) Effect of the composition on total triglycerids plasma levels;
5°) Effect of the composition on lipoperoxides plasma levels. 70 Male rats, each weighing 180–200 g, were used.

The animals were divided in 7 groups of 10 animals each:

1° group: Controls:
   10 animals (control at time 0) were used without treatments, 10 animals (control after 20 day diet) were subjected for 20 days to standard hypertriglyceridemizing and hypercholesterolemizing hypercaloric diet consisting of: casein: 20%; mixture of oligoelements and mineral salts: 3.5%; mixture of vitamins: 0.1%; choline ditartrate: 0.2%; cellulose: 5%; cholesterol: 0.5%; sodium cholate: 0.25%; saccharose: 55.44% and lard: 14.9%.

2° group: Treated with lipase- and amylase- inhibiting proteins:
   the animals were subjected for 20 days to the same diet as the controls except that 5 g of lipase- and amylase- inhibiting proteins (in the ratios and types as reported in example 3 above) replaced part of the proteins from casein (casein used: 15%)

3° group: Treated with egg lecithins:
   the animals were subjected for 20 days to the same diet as the controls except that 5 g of egg lecithin (in the ratios and types as reported in example 3 above) replaced part of the fats from lard (lard used: 9.9%)

4° group: Treated with the mixture of fibers:
   the animals were subjected for 20 days to the same diet as the controls except that 5 g of a mixture of fibers (in the ratios and types as reported in example 3 above) completely replaced the cellulose used in the control diet 5° group: Treated with the lioorotein complexes according to the invention:
   the animals were subjected for 20 days to the same diet as the controls except that 10 g of lipoprotein complexes according to the invention (consisting of 5 g of inhibiting proteins and 5 g of egg lecithins and prepared as described in example 3 above) replaced part of the proteins from casein and part of the fats from lard (casein used: 15%; lard used: 9.9%)

6° group: Treated with the compositions of the invention containing the lipoTorotein complexes in combination with a polysaccharide component:
   the animals were subjected for 20 days to the same diet as the controls except that 15 g of composition according to Example 3 replaced part of the proteins from casein (casein used: 15%), part of the fats from lard (lard used: 9.9%) and all of the cellulose present in the standard diet.

The obtained results are reported in Table I.

TABLE I

Body weight (expressed as percent increase against time 0); levels of total cholesterol, HDL cholesterol, triglycerids and lipoperoxides in rat plasma before and after 20 day dietetic treatments

| | Body weight (% increase) | Total cholesterol (mg dl$^{-1}$) | HDL cholesterol (mg dl$^{-1}$) | Total triglycerides (mg dl$^{-1}$) | Plasmatic lipoperoxides (malonyldialdehyde mmoles per ml)* |
|---|---|---|---|---|---|
| Control rats at time 0 | — | 36.1 ± 2.9 | 25.4 ± 2.3 | 49.5 ± 7.4 | 2.6 ± 0.5 |
| Control rats after 20 day diet | +24.4 ± 4.2% | 118.4 ± 14.5 | 31.6 ± 4.2 | 87.4 ± 14.1 | 6.2 ± 0.9 |
| 2° group: treated with proteins | +21.7 ± 3.8% | 115.5 ± 15.6 | 32.5 ± 3.4 | 86.8 ± 10.5 | 6.0 ± 0.9 |
| 3° group: treated with lecithins | +26.4 ± 4.1% | 110.9 ± 14.7 | 31.8 ± 4.7 | 87.7 ± 13.8 | 6.1 ± 1.2 |
| 4° group: treated with fibers | +23.2 ± 4.8% | 115.5 ± 12.8 | 32.5 ± 3.8 | 86.9 ± 15.2 | 6.1 ± 1.4 |
| 5° group: treated with proteins and lecithins | +18.5 ± 2.8% | 96.8 ± 10.5 | 33.6 ± 5.0 | 78.6 ± 14.5 | 4.8 ± 0.8 |
| 6° group: treated with proteins, lecithins and fibers | +13.4 ± 1.9% | 85.7 ± 12.4 | 33.9 ± 3.9 | 75.8 ± 12.7 | 4.1 ± 0.6 |

*Malonyldialdehyde is dosed according to the procedure by K. Yagi et al., 1982, in "Lipid Peroxides in Biology and Medicine, Academic Press, New York, pages 324–340.

The data of Table I evidence that the administrations of the lipoprotein complexes (compositions of lipase- and/or amylase-inhibiting proteins and phospholipids) or of the compositions containing the lipoprotein complexes in combination with a polysaccharide component (compositions of fibers, lipase- and/or amylase-inhibiting proteins and phospholipids) are capable of significantly limiting the increase in body weight and of promoting a significant decrease in cholesterol, triglycerids and lipoperoxides plasma levels. Said decrease both in the case of binary and ternary mixtures, is by far higher than the sum of the decreases obtainable by administering the single components separately.

The addition of fibers, such as chitosan, lignins and derivatives and/or, optionally, of many other species of vegetable fibers to binary mixtures consisting of lipoprotein complexes of the inhibiting proteins and phospholipids involves the further advantage of remarkably preventing or reducing some mild disorders of the gastrointestinal tract, such as diarrhoea, aerophagia, abdominal pain and distension, which can, although rarely, be induced by the lipoprotein complexes.

The controlling activity on body weight increase and the other specific hypolipidemizing and antioxidizing activities of the binary and/or ternary compositions of the invention, when administered during meals, can further be increased by separately administering, between meals, supplements containing one or more basic lipophilic nutrients, such as antioxidant vitamins (vitamin E, tocotrienols, vitamin A and carotenes, vitamin D, etc.).

What is claimed is:

1. A lipoprotein complex comprising
    a lipase-inhibiting protein or peptide component, and/or
    an amylase-inhibiting protein or peptide component, and
    a phospholipid component.

2. A lipoprotein complex as claimed in claim 1, comprising a lipase-inhibiting protein or peptide component and a phospholipid component.

3. A lipoprotein complex as claimed in claim 1, comprising 10 to 40% by weight of said lipase-inhibiting protein or peptide component, 10 to 40% by weight of said amylase-inhibiting protein or peptide component and 20 to 80% by weight of said phospholipid component.

4. A lipoprotein complex as claimed in claim 1, in which said lipase-inhibiting protein or peptide is obtained by extraction from vegetable materials selected from wheat flour and soy-bean, or animal materials selected from serum or egg albumins, lactoglobulins, myoglobins.

5. A lipoprotein complex as claimed in claim 1, in which said amylase-inhibiting protein or peptide component is obtained by extraction from materials vegetable including cereals and legumes.

6. A lipoprotein complex as claimed in claim 1, in which said phospholipid component is selected from the group consisting of: phosphatidylcholine, phosphatidylethanolamine, mono- and dimetilphosphatidylethanolamine, phosphatidylserine, phosphatidylinositol and derivatives, phosphatidylglycerol, cardiolipins, lysophospholipid analogues of the above compounds and mixtures thereof.

7. A process for the preparation of a lipoprotein complex as claimed in claim 1, comprising the following steps:
    adhering said phospholipid component to carrier particles, to obtain phospholipid-film coated particles,
    adding said particles with an aqueous buffered solution containing said lipase- and amylase-inhibiting protein or peptide components, while stirring for 20–60 minutes,
    centrifuging to separate the particles from the supernatant, which is spray-dried to obtain said lipoprotein complex in the form of a powder.

8. A process as claimed in claim 7, in which said phospholipid component is adhered to said particles by evaporating a solution of the phospholipid component in an organic solvent containing said particles.

9. A process as claimed in claim 7, in which said inert carrier particles are glass microbeads.

10. A process for the preparation of a lipoprotein complex as claimed in claim 1, comprising the following steps:
    dissolving said phospholipid component in a hot alcoholic solvent
    mixing the resulting alcoholic solution with an equal or larger volume of a buffered aqueous solution containing said lipase- and amylase-inhibiting protein or peptide components, while stirring at 0–4° C. for 1–30 minutes,
    spray-drying the resulting mixture, to obtain said lipoprotein complex in the form of a powder.

11. A composition comprising a lipoprotein complex as claimed in claim 1 and a polysaccharide component selected from the group consisting of starches, flours, celluloses, alimentary fibers, chitins, chitosans, pectins, inulins, lignins and derivatives, cyclodextrins and derivatives and mixtures thereof.

12. A composition as claimed in claim 11, in which said lipoprotein complex and said polysaccharide component are present in a weight ratio ranging from 2:1 to 1:100.

13. A process for the preparation of a composition as claimed in claim 11, comprising the steps of:
    dissolving said phospholipid component in a hot alcoholic solvent,
    mixing the resulting alcoholic solution with an equal or larger volume of a buffered aqueous solution containing said lipase- and amylase-inhibiting protein or peptide components while stirring at 0–4° C. for 1–30 minutes,
    adding said polysaccharide component under stirring at 20–25° C.,
    spray-drying the mixture, to obtain said composition in the form of a powder.

14. A lipoprotein complex comprising
    an amylase-inhibiting protein or peptide component, and
    a phospholipid component.

15. A method for treatment of hypercholesterolemia comprising the steps of:
    (1) providing a lipoprotein complex comprising
        a lipase-inhibiting protein or peptide component, and/or
        an amylase-inhibiting protein or peptide component, and
        a phospholipid component; and
    (2) administering to a human in need thereof a therapeutically effective amount of the lipoprotein complex.

16. A method for treatment of hypertriglyceridemia comprising the steps of:
    (1) providing a lipoprotein complex comprising
        a lipase-inhibiting protein or peptide component, and/or
        an amylase-inhibiting protein or peptide component, and
        a phospholipid component; and
    (2) administering to a human in need thereof a therapeutically effective amount of the lipoprotein complex.

17. A method of treatment of hypercholesterolemia comprising the steps of:

(1) providing a composition comprising:
   (a) a lipoprotein complex comprising a lipase-inhibiting protein or peptide component, and/or
   an amylase-inhibiting protein or peptide component, and
   a phospholipid component, and
   (b) a polysaccharide component selected from the group consisting of starches, flours, celluloses, alimentary fibers, chitins, chitosans, pectins, inulins, lignins and derivatives, cyclodextrins and derivatives and mixtures thereof; and
(2) administering to a human in need thereof a therapeutically effective amount of the composition.

18. A method of treatment of hypertriglyceridemia comprising the steps of:
(1) providing a composition comprising:
   (a) a lipoprotein complex comprising a lipase-inhibiting protein or peptide component, and/or
   an amylase-inhibiting protein or peptide component, and
   a phospholipid component, and
   (b) a polysaccharide component selected from the group consisting of starches, flours, celluloses, alimentary fibers, chitins, chitosans, pectins, inulins, lignins and derivatives, cyclodextrins and derivatives and mixtures thereof; and
(2) administering to a human in need thereof a therapeutically effective amount of the composition.

19. A therapeutic method comprising the steps of:
(1) providing a lipoprotein complex comprising
   a lipase-inhibiting protein or peptide component, and/or
   an amylase-inhibiting protein or peptide component, and
   a phospholipid component; and
(2) administering to a human in need thereof a therapeutically effective amount of the lipoprotein complex.

20. A therapeutic method comprising the steps of:
(1) providing a composition comprising:
   (a) a lipoprotein complex comprising a lipase-inhibiting protein or peptide component, and/or
   an amylase-inhibiting protein or peptide component, and
   a phospholipid component, and
   (b) a polysaccharide component selected from the group consisting of starches, flours, celluloses, alimentary fibers, chitins, chitosans, pectins, inulins, lignins and derivatives, cyclodextrins and derivatives and mixtures thereof; and
(2) administering to a human in need thereof a therapeutically effective amount of the composition.

21. A method for treatment of obesity and overweight, comprising the steps of:
(1) providing a lipoprotein complex comprising
   a lipase-inhibiting protein or peptide component, and/or
   an amylase-inhibiting protein or peptide component, and
   a phospholipid component: and
(2) administering to a human in need thereof a therapeutically effective amount of the lipoprotein complex.

22. A method of treatment of obesity and overweight, comprising the steps of:

(1) providing a composition comprising:
   (a) a lipoprotein complex comprising a lipase-inhibiting protein or peptide component, and/or
   an amylase-inhibiting protein or peptide component, and
   a phospholipid component, and
   (b) a polysaccharide component selected from the group consisting of starches, flours, celluloses, alimentary fibers, chitins, chitosans, pectins, inulins, lignins and derivatives, cyclodextrins and derivatives and mixtures thereof; and
(2) administering to a human in need thereof an therapeutically effective amount of the composition.

23. A method of administering a lipoprotein complex comprising a lipase-inhibiting protein or peptide component, and/or an amylase-inhibiting protein or peptide component, and a phospholipid component, comprising the steps of:
   formulating the lipoprotein complex as an alimentary supplement; and
   administering the alimentary supplement of a human being.

24. A method of administering a composition comprising
   (a) a lipoprotein complex comprising a lipase-inhibiting protein or peptide component, and/or
   an amylase-inhibiting protein or peptide component, and
   a phospholipid component, and
   (b) a polysaccharide component selected from the group consisting of starches, flours, celluloses, alimentary fibers, chitins, chitosans, pectins, inulins, lignins and derivatives, cyclodextrins and derivatives and mixtures thereof;
   said method comprising the steps of formulating the composition as alimentary supplement; and
   administering the alimentary supplement to a human being.

25. A method for avoiding excessive weight increase, comprising the steps of:
(1) providing a lipoprotein complex comprising lipase-inhibiting protein or peptide component, and/or an amylase-inhibiting protein or peptide component, and a phospholipid component; and
(2) administering the complex daily to a human in amounts ranging from 0.02 to 3000 mg, preferably 10–200 mg, per kg body weight.

26. A method for avoiding excessive weight increase, comprising the steps of:
(1) providing a composition comprising:
   (a) a lipoprotein complex comprising
   a lipase-inhibiting protein or peptide component, and/or
   an amylase-inhibiting protein or peptide component, and
   a phospholipid component, and
   (b) a polysaccharide component selected from the group consisting of starches, flours, celluloses, alimentary fibers, chitins, chitosans, pectins, inulins, lignins and derivatives, cyclodextrins and derivatives and mixtures thereof; and
(2) administering the complex daily to a human in amounts ranging from 0.03 to 5000 mg, preferably 15–300 mg, per kg body weight.

27. A pharmaceutical formulation, comprising:
(1) a lipoprotein complex comprising
   a lipase-inhibiting protein or peptide component, and/or an amylase-inhibiting protein or peptide component, and a phospholipid component; and (2) a pharmaceutically-acceptable carrier.

28. A pharmaceutical formulation comprising (1) a composition comprising
  (a) a lipoprotein complex comprising a lipase-inhibiting protein or peptide component, and/or
  an amylase-inhibiting protein or peptide component, and
  a phospholipid component; and
  (b) a polysaccharide component selected from the group consisting of starches, flours, celluloses, alimentary fibers, chitins, chitosans, pectins, inulins, lignins and derivatives, cyclodextrins and derivatives and mixtures thereof: and (2) a pharmaceutically-acceptable carrier.

29. An alimentary and dietetic product containing a lipoprotein complex comprising:

a lipase-inhibiting protein or peptide component; and/or an amylase-inhibiting protein or peptide component; and a phospholipid component.

30. An alimentary and dietetic product containing a composition comprising:

(a) a lipoprotein complex comprising a lipase-inhibiting protein or peptide component, and/or an amylase-inhibition protein or peptide component, and a phospholipid component, and (b) a polysaccharide component selected from the group consisting of starches, flours, celluloses, alimentary fibers, chitins, chitosans, pectins, inulins, lignins and derivatives cyclodextrins and derivatives and mixtures thereof.

* * * * *